US007713637B2

(12) United States Patent
Kleiner et al.

(10) Patent No.: US 7,713,637 B2
(45) Date of Patent: May 11, 2010

(54) COATING CONTAINING PEGYLATED HYALURONIC ACID AND A PEGYLATED NON-HYALURONIC ACID POLYMER

(75) Inventors: Lothar W. Kleiner, Los Altos, CA (US); Connie S. Kwok, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1098 days.

(21) Appl. No.: 11/367,561

(22) Filed: Mar. 3, 2006

(65) Prior Publication Data

US 2007/0207181 A1    Sep. 6, 2007

(51) Int. Cl.
  B32B 27/06    (2006.01)
  B32B 27/30    (2006.01)
  B32B 27/36    (2006.01)
  A61F 2/02     (2006.01)
  A61F 2/04     (2006.01)
(52) U.S. Cl. ............... 428/522; 428/480; 428/532; 623/1.42; 623/1.46; 623/13.18; 623/23.57; 623/23.58; 623/23.59; 623/23.7; 623/23.75; 424/423; 424/78.3; 536/55.1; 514/54; 525/54.2; 525/54.1; 525/54.23
(58) Field of Classification Search .................. None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |

(Continued)

FOREIGN PATENT DOCUMENTS

DE    42 24 401    1/1994

(Continued)

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

(Continued)

Primary Examiner—Vivian Chen
(74) Attorney, Agent, or Firm—Squire Sanders & Dempsey LLP

(57) ABSTRACT

Provided herein are a coating or a device (e.g., absorbable stent) that includes a PEGylated hyaluronic acid and a PEGylated non-hyaluronic acid biocompatible polymer and the methods of use thereof.

17 Claims, No Drawings

U.S. PATENT DOCUMENTS

| | | | |
|---|---|---|---|
| 5,667,767 A | 9/1997 | Greff et al. | |
| 5,670,558 A | 9/1997 | Onishi et al. | |
| 5,674,242 A | 10/1997 | Phan et al. | |
| 5,679,400 A | 10/1997 | Tuch | |
| 5,700,286 A | 12/1997 | Tartaglia et al. | |
| 5,702,754 A | 12/1997 | Zhong | |
| 5,711,958 A | 1/1998 | Cohn et al. | |
| 5,716,981 A | 2/1998 | Hunter et al. | |
| 5,721,131 A | 2/1998 | Rudolph et al. | |
| 5,723,219 A | 3/1998 | Kolluri et al. | |
| 5,735,897 A | 4/1998 | Buirge | |
| 5,746,998 A | 5/1998 | Torchilin et al. | |
| 5,759,205 A | 6/1998 | Valentini | |
| 5,776,184 A | 7/1998 | Tuch | |
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,857,998 A | 1/1999 | Barry | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,111,014 A * | 8/2000 | Wang et al. | 525/64 |
| 6,113,629 A | 9/2000 | Ken | |
| 6,117,947 A * | 9/2000 | Wang et al. | 525/404 |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 * | 7/2001 | Yang et al. | 623/1.46 |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,368,658 B1 * | 4/2002 | Schwarz et al. | 427/2.15 |
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,475,779 B2 | 11/2002 | Mathiowitz et al. | |
| 6,476,156 B1 * | 11/2002 | Kim et al. | 525/403 |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 * | 7/2003 | Hossainy et al. | 623/1.45 |
| 6,585,926 B1 | 7/2003 | Mirzaee | |
| 6,605,154 B1 | 8/2003 | Villareal | |
| 6,613,432 B2 | 9/2003 | Zamora et al. | |
| 6,616,765 B1 | 9/2003 | Wu et al. | |
| 6,620,617 B2 | 9/2003 | Mathiowitz et al. | |
| 6,623,448 B2 | 9/2003 | Slater | |

| | | | | | | |
|---|---|---|---|---|---|---|
| 6,625,486 B2 | 9/2003 | Lundkvist et al. | | 2003/0028244 A1 | 2/2003 | Bates et al. |
| 6,632,446 B1 * | 10/2003 | Hubbell et al. ............... 424/423 | | 2003/0032767 A1 | 2/2003 | Tada et al. |
| 6,638,538 B1 * | 10/2003 | Hashimoto et al. .......... 424/548 | | 2003/0036794 A1 | 2/2003 | Ragheb et al. |
| 6,641,611 B2 | 11/2003 | Jayaraman | | 2003/0039689 A1 | 2/2003 | Chen et al. |
| 6,645,135 B1 | 11/2003 | Bhat | | 2003/0040790 A1 | 2/2003 | Furst |
| 6,645,195 B1 | 11/2003 | Bhat et al. | | 2003/0059520 A1 | 3/2003 | Chen et al. |
| 6,656,216 B1 | 12/2003 | Hossainy et al. | | 2003/0060877 A1 | 3/2003 | Falotico et al. |
| 6,656,506 B1 | 12/2003 | Wu et al. | | 2003/0065377 A1 | 4/2003 | Davila et al. |
| 6,660,034 B1 | 12/2003 | Mandrusov et al. | | 2003/0072868 A1 | 4/2003 | Harish et al. |
| 6,663,662 B2 | 12/2003 | Pacetti et al. | | 2003/0073961 A1 | 4/2003 | Happ |
| 6,663,880 B1 | 12/2003 | Roorda et al. | | 2003/0083646 A1 | 5/2003 | Sirhan et al. |
| 6,666,880 B1 | 12/2003 | Chiu et al. | | 2003/0083739 A1 | 5/2003 | Cafferata |
| 6,673,154 B1 | 1/2004 | Pacetti et al. | | 2003/0097088 A1 | 5/2003 | Pacetti |
| 6,673,385 B1 | 1/2004 | Ding et al. | | 2003/0097173 A1 | 5/2003 | Dutta |
| 6,689,099 B2 | 2/2004 | Mirzaee | | 2003/0099712 A1 | 5/2003 | Jayaraman |
| 6,689,350 B2 | 2/2004 | Uhrich | | 2003/0105518 A1 | 6/2003 | Dutta |
| 6,695,920 B1 | 2/2004 | Pacetti et al. | | 2003/0113439 A1 | 6/2003 | Pacetti et al. |
| 6,706,013 B1 | 3/2004 | Bhat et al. | | 2003/0150380 A1 | 8/2003 | Yoe |
| 6,709,514 B1 | 3/2004 | Hossainy | | 2003/0157241 A1 | 8/2003 | Hossainy et al. |
| 6,712,845 B2 | 3/2004 | Hossainy | | 2003/0158517 A1 | 8/2003 | Kokish |
| 6,713,119 B2 | 3/2004 | Hossainy et al. | | 2003/0190406 A1 | 10/2003 | Hossainy et al. |
| 6,716,444 B1 | 4/2004 | Castro et al. | | 2003/0207020 A1 | 11/2003 | Villareal |
| 6,723,120 B2 | 4/2004 | Yan | | 2003/0211230 A1 | 11/2003 | Pacetti et al. |
| 6,730,064 B2 | 5/2004 | Ragheb et al. | | 2004/0018296 A1 | 1/2004 | Castro et al. |
| 6,733,768 B2 | 5/2004 | Hossainy et al. | | 2004/0029952 A1 | 2/2004 | Chen et al. |
| 6,740,040 B1 | 5/2004 | Mandrusov et al. | | 2004/0047978 A1 | 3/2004 | Hossainy et al. |
| 6,743,462 B1 | 6/2004 | Pacetti | | 2004/0047980 A1 | 3/2004 | Pacetti et al. |
| 6,746,773 B2 | 6/2004 | Llanos et al. | | 2004/0052858 A1 | 3/2004 | Wu et al. |
| 6,749,626 B1 | 6/2004 | Bhat et al. | | 2004/0052859 A1 | 3/2004 | Wu et al. |
| 6,753,071 B1 | 6/2004 | Pacetti et al. | | 2004/0054104 A1 | 3/2004 | Pacetti |
| 6,758,859 B1 | 7/2004 | Dang et al. | | 2004/0060508 A1 | 4/2004 | Pacetti et al. |
| 6,759,054 B2 | 7/2004 | Chen et al. | | 2004/0062853 A1 | 4/2004 | Pacetti et al. |
| 6,764,505 B1 | 7/2004 | Hossainy et al. | | 2004/0063805 A1 | 4/2004 | Pacetti et al. |
| 6,776,796 B2 | 8/2004 | Falotico et al. | | 2004/0071861 A1 | 4/2004 | Mandrusov et al. |
| 6,780,424 B2 | 8/2004 | Claude | | 2004/0072922 A1 | 4/2004 | Hossainy et al. |
| 6,790,228 B2 | 9/2004 | Hossainy et al. | | 2004/0073298 A1 | 4/2004 | Hossainy |
| 6,824,559 B2 | 11/2004 | Michal | | 2004/0086542 A1 | 5/2004 | Hossainy et al. |
| 6,861,088 B2 | 3/2005 | Weber et al. | | 2004/0086550 A1 | 5/2004 | Roorda et al. |
| 6,865,810 B2 | 3/2005 | Stinson | | 2004/0096504 A1 | 5/2004 | Michal |
| 6,869,443 B2 | 3/2005 | Buscemi et al. | | 2004/0098117 A1 | 5/2004 | Hossainy et al. |
| 6,878,160 B2 | 4/2005 | Gilligan et al. | | 2004/0175406 A1 * | 9/2004 | Schwarz ..................... 424/423 |
| 6,887,270 B2 * | 5/2005 | Miller et al. ............. 623/11.11 | | 2004/0224001 A1 * | 11/2004 | Pacetti et al. ................ 424/423 |
| 6,887,485 B2 | 5/2005 | Fitzhugh et al. | | 2005/0037052 A1 | 2/2005 | Udipi et al. |
| 6,890,546 B2 | 5/2005 | Mollison et al. | | 2005/0038134 A1 | 2/2005 | Loomis et al. |
| 6,890,583 B2 | 5/2005 | Chudzik et al. | | 2005/0038497 A1 | 2/2005 | Neuendorf et al. |
| 6,899,731 B2 | 5/2005 | Li et al. | | 2005/0043786 A1 | 2/2005 | Chu et al. |
| 6,998,456 B1 * | 2/2006 | Mallapragada et al. ... 526/328.5 | | 2005/0049693 A1 | 3/2005 | Walker |
| 7,008,667 B2 | 3/2006 | Chudzik et al. | | 2005/0049694 A1 | 3/2005 | Neary |
| 7,063,884 B2 * | 6/2006 | Hossainy et al. ............ 428/212 | | 2005/0054774 A1 | 3/2005 | Kangas |
| 7,311,980 B1 * | 12/2007 | Hossainy et al. ............ 428/480 | | 2005/0055044 A1 | 3/2005 | Kangas |
| 7,329,413 B1 * | 2/2008 | Pacetti et al. ................ 424/423 | | 2005/0055078 A1 | 3/2005 | Campbell |
| 7,387,810 B2 * | 6/2008 | Hossainy ..................... 427/2.1 | | 2005/0060020 A1 | 3/2005 | Jenson |
| 7,456,275 B2 * | 11/2008 | Shimoboji .................. 536/55.1 | | 2005/0064088 A1 | 3/2005 | Fredrickson |
| 2001/0007083 A1 | 7/2001 | Roorda | | 2005/0065501 A1 | 3/2005 | Wallace |
| 2001/0029351 A1 | 10/2001 | Falotico et al. | | 2005/0065545 A1 | 3/2005 | Wallace |
| 2001/0037145 A1 | 11/2001 | Guruwaiya et al. | | 2005/0065593 A1 | 3/2005 | Chu et al. |
| 2002/0005206 A1 | 1/2002 | Falotico et al. | | 2005/0074406 A1 | 4/2005 | Couvillon et al. |
| 2002/0007213 A1 | 1/2002 | Falotico et al. | | 2005/0074545 A1 | 4/2005 | Thomas |
| 2002/0007214 A1 | 1/2002 | Falotico | | 2005/0075714 A1 | 4/2005 | Cheng et al. |
| 2002/0007215 A1 | 1/2002 | Falotico et al. | | 2005/0079274 A1 | 4/2005 | Palasis et al. |
| 2002/0051730 A1 | 5/2002 | Bodnar et al. | | 2005/0084515 A1 | 4/2005 | Udipi et al. |
| 2002/0077693 A1 | 6/2002 | Barclay et al. | | 2005/0106210 A1 | 5/2005 | Ding et al. |
| 2002/0082679 A1 | 6/2002 | Sirhan et al. | | 2005/0112170 A1 * | 5/2005 | Hossainy et al. ............ 424/423 |
| 2002/0087123 A1 | 7/2002 | Hossainy et al. | | 2005/0113903 A1 | 5/2005 | Rosenthal et al. |
| 2002/0091433 A1 | 7/2002 | Ding et al. | | 2005/0123505 A1 * | 6/2005 | Chen et al. ............... 424/78.27 |
| 2002/0111590 A1 | 8/2002 | Davila et al. | | 2005/0164980 A1 * | 7/2005 | Shimoboji ................... 514/54 |
| 2002/0165608 A1 | 11/2002 | Llanos et al. | | 2005/0169957 A1 * | 8/2005 | Hossainy ..................... 424/423 |
| 2002/0176849 A1 | 11/2002 | Slepian | | 2005/0244363 A1 * | 11/2005 | Hossainy et al. ............ 424/78.3 |
| 2002/0183581 A1 | 12/2002 | Yoe et al. | | | | |
| 2002/0188037 A1 | 12/2002 | Chudzik et al. | | FOREIGN PATENT DOCUMENTS | | |
| 2002/0188277 A1 | 12/2002 | Roorda et al. | | | | |
| 2003/0004141 A1 | 1/2003 | Brown | | EP | 0 301 856 | 2/1989 |
| 2003/0028243 A1 | 2/2003 | Bates et al. | | EP | 0 396 429 | 11/1990 |

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 6/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 10/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/022603 | 3/2004 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methactylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies, Progress in Cardiovascular Diseases*, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685- 694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan*, Novel Endothelin Receptor, Chemical Abstract 125:212307 (1996).

van Beusekom et al., *Coronary stent coatings, Coronary Artery Disease* 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

International Search Report for PCT/US2007/004558, filed Feb. 15, 2007, mailed Aug. 2, 2007, 12 pgs.

* cited by examiner

COATING CONTAINING PEGYLATED HYALURONIC ACID AND A PEGYLATED NON-HYALURONIC ACID POLYMER

BACKGROUND OF THE INVENTION

1. Field of the Invention

This invention generally relates to a coating or a medical device such as stent formed of a PEGylated hyaluronic acid (HA) and a PEGylated non-HA polymer.

2. Description of the Background

A current paradigm in the art of stenting is to use biomaterials to modulate biological responses to the implant surface. One of the biomaterials is hyaluronic acid (HA). Due to HA's hydrophilicity, it is often modified for the ease of manufacture process. One of the modification methods is to modify HA with PEG and/or adding positive charge tridodecyl methyl ammonium chloride (TDMAC) to neutralize the negative charges of HA to make the HA dissolvable in an organic solvent. However, a coating formed of such derivatized HA often lacks the mechanical properties required of the coating for an implantable device (e.g., a stent).

The present invention provides embodiments as follows to address the above-identified needs and problems.

SUMMARY OF THE INVENTION

The present invention provides for a polymer blend that includes a PEGylated HA and a PEGylated non-HA polymer. The polymer defined herein can be used alone or in combination with another biocompatible polymer and/or a biobeneficial material to form coatings on implantable medical devices or to form the implantable medical devices themselves. The polymers or polymer blends described herein can also be used to form the implantable device itself. The implantable device can optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl -rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication anastomotic proliferation for vein and artificial grafts, bile duct obstruction, ureter obstruction, tumor obstruction, or combinations thereof.

DETAILED DESCRIPTION

The present invention provides for a polymer blend that includes a PEGylated HA and a PEGylated non-HA polymer. The polymer defined herein can be used alone or in combination with another biocompatible polymer and/or a biobeneficial material to form coatings on implantable medical devices or to form the implantable medical devices themselves. The coating or device can optionally include one or more other biocompatible polymers. The coating or device can optionally include one or more biobeneficial materials. Further, the coating or device can optionally include one or more bioactive agents.

The PEGylated HA and the PEGylated non-HA polymer can be used in the ratio (PEGylated HA/PEGylated non-HA) of between about 0.01:0.99 and about 0.99:0.01, between about 0.1:0.9 and about 0.9:0.1, between about 0.2:0.0.8 and about 0.8:0.2, between about 0.3:0.7 and about 0.7:0.3, or between about 0.4:0.6 and about 0.6:0.4 or of about 0.5:0.5.

A device having a coating described herein can be used to treat, prevent, or ameliorate disorder such as atherosclerosis, thrombosis, restenosis, hemorrhage, vascular dissection or perforation, vascular aneurysm, vulnerable plaque, chronic total occlusion, claudication anastomotic proliferation for vein and artificial grafts, bile duct obstruction, ureter obstruction, tumor obstruction, or combinations thereof.

PEGylated HA

The term hyaluronic acid (HA) includes HA molecules, fragments, and derivatives thereof. In particular, the term HA and HA fragments as used herein refers to any molecules that have a unit or repeating units as shown in Formula I:

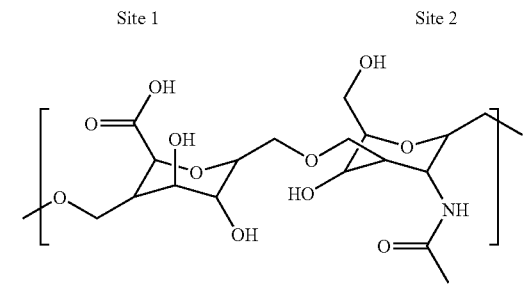

Formula I

Depending on the number of the units of Formula I present, the HA can have a weight-average molecule weight ($M_w$) in the range from about 250 Daltons to about 10,000,000 Daltons, e.g., about 500 Daltons to about 1,000,000 Daltons, about 1000 Daltons to about 500,000 Daltons, about 2,000 Daltons to about 400,000 Daltons, about 5,000 Daltons to about 300,000 Daltons, about 10,000 Daltons to about 200,000 Daltons, about 10,000 Daltons to about 100,000 Daltons, about 10,000 Daltons to about 75,000 Daltons, or about 10,000 Daltons to about 50,000 Daltons. Some embodiments specifically exclude one or more HA or HA fragments having the molecular weight ranges described herein.

As used herein, the term PEGylated refers to being modified with poly(ethylene glycol) (PEG) or a molecule of the similar nature via a covalent bond or non-covalent force such as ionic interaction or hydrogen bonding. Molecules similar to PEG in nature include, but are not limited to, poly(olefin glycol) such as polypropylene glycol, poly(olefin oxide) such as poly(ethylene oxide or poly(propylene oxide), or a copolymer having a PEG block, a poly(olefin glycol) block, and/or a poly(olefin oxide) block such as PLURONIC™ surfactants (polypropylene oxide-co-polyethylene glycol) or poly(tetramethylene glycol).

The PEG molecules as used herein have a weight average molecular weight ($M_w$) preferably below about 50,000 Daltons, e.g., in the range from about 100 Daltons to about 50,000 Daltons, about 150 Daltons to about 45,000 Daltons, about 300 Daltons to about 45,000 Daltons, about 500 Daltons to about 45,000 Daltons, about 750 Daltons to about 45,000 Daltons, about 1,000 Daltons to about 45,000 Daltons, about 1,500 Daltons to about 45,000 Daltons, about 3,000 Daltons to about 45,000 Daltons, about 5,000 Daltons to about 45,000 Daltons, about 7,500 Daltons to about 45,000 Daltons, about 10,000 Daltons to about 45,000 Daltons, about 15,000 Daltons to about 45,000 Daltons, about 20,000 Daltons to about 45,000 Daltons, about 25,000 Daltons to about 45,000 Daltons, about 30,000 Daltons to about 45,000 Daltons, about 35,000 Daltons to about 45,000 Daltons, about 40,000 Daltons to about 45,000 Daltons. Some embodiments specifically exclude one or more PEG molecules having the molecular weight ranges described herein.

In some embodiments, the PEGylated HA described herein can have a weight average molecular weight ($M_w$) in the range from about 250 Daltons to about 10,000,000 Daltons, e.g., about 500 Daltons to about 1,000,000 Daltons, about 1000 Daltons to about 500,000 Daltons, about 2,000 Daltons to about 400,000 Daltons, about 5,000 Daltons to about 300,000 Daltons, about 10,000 Daltons to about 200,000 Daltons, about 10,000 Daltons to about 100,000 Daltons, about 10,000 Daltons to about 75,000 Daltons, or about 10,000 Daltons to about 50,000 Daltons. In some embodiments, the PEGylated HA can have a molecular weight in the range from about 70,000 Daltons to about 320,000 Daltons. Some embodiments specifically exclude one or more PEGylated HA or HA fragments having the molecular weight ranges described herein.

PEGylated Non-HA Polymer

The term PEGylated non-HA polymer, as used herein, refers to any biocompatible polymer modified with a PEG molecule. The modification by PEG molecule of the biocompatible polymer can be in any form known in the art. For example, the PEGylated non-HA polymer can have PEG molecule in the backbone in the form of a block copolymer or random copolymer. Alternatively, the PEGylated non-HA polymer can have PEG molecules as pendant groups.

The non-HA polymer can be any biocompatible polymer commonly used in the art of medical or biomedical coating. Some examples of the non-HA polymer for forming the PEGylated non-HA polymer include, but are not limited to, poly(ester amide), polyacids, polyesters, polyhydroxyalkanoates (PHA), polycaprolactone, poly(lactide-co-caprolactone), poly(glycolide-co-caprolactone), poly(dioxanone), poly(ortho esters), poly(anhydrides), poly(tyrosine carbonates), poly(tyrosine arylates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyolefins, polyisobutylene and ethylene-alpha-olefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers, poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), copoly(ether-esters), hydroxy functional poly(vinyl pytrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the copolymer described herein can exclude any one of the aforementioned polymers.

The term PHA as used herein includes, but is not limited to, poly(2-hydroxyacids), poly(3-hydroxyacids), poly(4-hydroxyacids), and copolymers that include any of 2-hydroxyacids, 3-hydroxyacids, and/or 4-hydroxyacids. 2-hydroxyacids include, but are not limited to, lactic acid, glycolic acid and other hydroxyacids having a substituent on the second carbon position of the 2-hydroxyacid molecule. 3-Hydroxyacids include, but are not limited to, 3-hydroxypropanoic acid, 3-hydroxybutyric acid, 3-hydroxyvaleric acid, 3-hydropentanoic acid, 3-hydroxyhexanoic acid, or 3-hydroxyhepanoic acid and other hydroxyacids having a substituent on the third carbon position of the 3-hydroxyacid molecule. 4-Hydroxyacids include, but are not limited to, 4-hydroxybutyric acid, 4-hydroxyvaleric acid, 4-hydropentanoic acid, 4-hydroxyhexanoic acid, 4-hydroxyhepanoic acid, or 4-hydroxyoctanoic acid and other hydroxyacids having a substituent on the fourth carbon position of the 4-hydroxyacid molecule. Other polymers can be found in Polymeric Biomaterials, $2^{nd}$ edition, Severian Dumitriu, Ed., Marcel Dekker, 2001; and Biomaterials Science, An Introduction to Materials in Medicine, Ratner, Hoffman, Schoen and Lemmons, Eds. Academic Press, New York, 1996.

The hydroxyacids provided above, other than glycolic acid, are optically active and can include the L-enantiomer, the D-enantiomer, a blend of L-enantiomer and D-enantiomer, and a racemic mixture of the L-enantiomer and the D-enantiomer thereof. For example, the term PLA includes, but are not limited to, poly(D,L-lactide), poly(L-lactide), poly(L-lactide-co-D,L-lactide), poly(D,L-lactide-co-glycolide), or poly(L-lactide-co-glycolide).

Some examples of these PEGylated non-HA polymers include acrylate or methacrylate based polymers having a general formula of

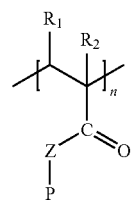

where $R_1$ and $R_2$ are independently H, methyl, ethyl, propyl, isopropyl, n-butyl, isobutyl, or phenyl, where Z is O, S, or $NR_3$ where $R_3$ is H, methyl, ethyl, propyl, isopropyl, n-butyl, isobutyl, or phenyl, where P is a PEG molecule, and where n is a positive integer ranging from 1 to 100,000.

Other examples of PEGylated non-HA polymers include PEGylated bioactive agents. Such bioactive agents or drugs can be a peptide, protein, antibody, or a drug. Examples of PEGylated proteins and peptides are PEGylated RGD peptide, PEGylated ANP peptide, PEGylated CNP peptide, and PEGylated osteopontin or combinations thereof. In some embodiments, such PEGylated bioactive agents include PEGylated matrix proteins. Examples of PEGylated drugs include PEGylated anti-proliferatives, PEGylated inflammatories, and combinations thereof.

Other examples PEGylated non-HA polymer include, but are not limited to, e.g. poly(ethylene oxide)/poly(lactic acid) (PEO/PLA), poly(styrene-isoprene-styrene)-PEG (SIS-PEG), polystyrene-PEG, polyisobutylene-PEG, polycaprolactone-PEG (PCL-PEG), poly(lactic acid-co-PEG) (PLA-PEG), poly(methyl methacryl ate)-PEG (PMMA-PEG), polydimethylsiloxane-co-PEG (PDMS-PEG), and poly(vinylidene fluoride)-PEG (PVDF-PEG).

In a preferred embodiment, the PEGylated non-HA polymer is PEGylated PLA or contains a PEGylated PLA block or moiety.

Non-HA Polymers

In some embodiments, the coating or absorbable device (e.g., absorbable stent) can optionally include one or more Non-HA polymers. The combination can be mixed, blended, or coated in separate layers. The additional biocompatible polymer can be biodegradable (both bioerodable or bioabsorbable) or nondegradable, and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilyl-propyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the copolymer described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

Biobeneficial Material

In some embodiments, a coating having the features described above can include a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the coating or device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly(ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), Pluronic™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, heparin, fragments and derivatives of heparin, glycosamino glycan (GAG), GAG derivatives, polysaccharide, elastin, chitosan, alginate, silicones, PolyActive™, and combinations thereof. In some embodiments, the coatings can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

Bioactive Agents

A coating described above can include any bioactive agent. The bioactive agent can be any bioactive agent, which is a therapeutic, prophylactic, or diagnostic agent. These agents can have anti-proliferative or anti-inflammatory properties or can have other properties such as antineoplastic, antiplatelet, anti-coagulant, anti-fibrin, antithrombotic, antimitotic, antibiotic, antiallergic, and antioxidant. The agents can be cytostatic agents, agents that promote the healing of the endothelium such as NO releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl) -rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro -arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), heart valve prostheses, cerebrospinal fluid shunts, pacemaker electrodes, catheters, endocardial leads (e.g., FINELINE and ENDOTAK, available from Guidant Corporation, Santa Clara, Calif.), anastomotic devices (e.g., CABG anastomotic clips) and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In some embodiments, the device is a absorbable stent.

Method of Use

In accordance with embodiments of the invention, a coating subjected to the treatment of a phase inversion process described above can be used to provided controlled release of a bioactive agent from a medical device (e.g., stent) during delivery and (in the case of a stent) expansion of the device, or thereafter, at a desired rate and for a predetermined time at the implantation site.

Preferably, the medical device is a stent. The stent described herein is useful for a variety of medical procedures, including, for example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A composition comprising a PEGylated hyaluronic acid (HA) and a PEGylated non-HA polymer,
    wherein the PEGylated HA and the non-HA polymer are independently modified with poly(ethylene glycol) (PEG), PEG like molecule or a combination thereof,
    wherein the PEGylated HA has a molecular weight in the range from about 7,000 Daltons to 320,000 Daltons, and
    wherein the PEGylated non-HA polymer is selected from the group consisting of PEGylated polyacrylates, PEGylated peptides, PEGylated proteins, and combinations thereof,
    wherein the PEG like molecule is selected from the group consisting of polyethers, polyglycols, polyalkylene oxides, and combinations thereof.

2. The composition of claim 1, wherein the PEGylated non-HA polymer is selected from the group consisting of PEGylated polyacrylates, PEGylated peptides, and PEGylated proteins.

3. An implantable device comprising a coating that comprises the composition of claim 2.

4. The composition of claim 1, wherein the PEGylated non-HA polymer further comprises PEGylated poly(lactic acid) (PLA).

5. An implantable device comprising a coating that comprises the composition of claim 4.

6. An implantable device comprising a coating that comprises the composition of claim 1.

7. A composition comprising a PEGylated hyaluronic acid (HA) and a PEGylated non-HA polymer;
    wherein the PEGylated HA and the non-HA polymer are independently modified with poly(ethylene glycol) (PEG), PEG like molecule or a combination thereof;
    wherein the PEGylated HA has a molecular weight in the range from about 7,000 Daltons to 320,000 Daltons; and
    wherein the PEG like molecule is selected from the group consisting of polyethers, polyglycols, polyalkylene oxides, and combinations thereof; and
    wherein the PEGylated non-HA polymer is

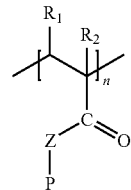

wherein R1 and R2 are independently H, methyl, ethyl, propyl, isopropyl, n-butyl, isobutyl, or phenyl,
    wherein Z is O, S, or $NR_3$ where $R_3$ is H, methyl, ethyl, propyl, isopropyl, n-butyl, isobutyl, or phenyl,
    wherein P is PEG or the PEG like molecule, and
    wherein n is a positive integer ranging from 1 to 100,000.

8. The composition of claim 7, wherein the PEG like molecule is selected from the group consisting of, polyglycols, polyalkylene oxides, and combinations thereof.

9. An implantable device comprising a coating that comprises the composition of claim 8.

10. The implantable device of claim 9, which is a stent.

11. The implantable device of claim 9, wherein the coating further comprises a bioactive agent.

12. The implantable device of claim 11, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and a combination thereof.

13. The implantable device of claim 12, which is a stent.

14. The composition of claim 7, wherein the PEG molecule has a weight average molecular weight ($M_w$) below about 45,000 Daltons.

15. An implantable device comprising a coating that comprises the composition of claim 14.

16. An implantable device comprising a coating that comprises the composition of claim 7.

17. An absorbable stent formed of the composition of claim 7.

* * * * *

UNITED STATES PATENT AND TRADEMARK OFFICE
CERTIFICATE OF CORRECTION

PATENT NO. : 7,713,637 B2
APPLICATION NO. : 11/367561
DATED : May 11, 2010
INVENTOR(S) : Lothar W. Kleiner et al.

It is certified that error appears in the above-identified patent and that said Letters Patent is hereby corrected as shown below:

In the Claims:

Column 10, line 4, cancel the text beginning with "1. A composition" to and ending "and combinations thereof." in column 10, line 17, and insert the following claim:

1. A composition comprising a PEGylated hyaluronic acid (HA) and a PEGylated non-HA polymer,
   wherein the PEGylated HA and the non-HA polymer are independently modified with poly(ethylene glycol) (PEG), PEG like molecule or a combination thereof,
   wherein the PEGylated HA has a molecular weight in the range from about 70,000 Daltons to 320,000 Daltons,
   wherein the PEGylated non-HA polymer is selected from the group consisting of PEGylated polyacrylates, PEGylated peptides, PEGylated proteins, and combinations thereof, and
   wherein the PEG like molecule is selected from the group consisting of polyethers, polyglycols, polyalkylene oxides, and combinations thereof.

Signed and Sealed this
Thirteenth Day of August, 2013

Teresa Stanek Rea
*Acting Director of the United States Patent and Trademark Office*

CERTIFICATE OF CORRECTION (continued)
U.S. Pat. No. 7,713,637 B2

In the Claims:

Column 10, line 31, cancel the text beginning with "1. A composition" to and ending "and combinations thereof." in column 10, line 58, and insert the following claim:

7. A composition comprising a PEGylated hyaluronic acid (HA) and a PEGylated non-HA polymer;
   wherein the PEGylated HA and the non-HA polymer are independently modified with poly(ethylene glycol) (PEG), PEG like molecule or a combination thereof;
   wherein the PEGylated HA has a molecular weight in the range from about 70,000 Daltons to 320,000 Daltons; and
   wherein the PEG like molecule is selected from the group consisting of polyethers, polyglycols, polyalkylene oxides, and combinations thereof; and
   wherein the PEGylated non-HA polymer is

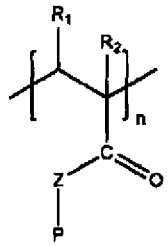

wherein R1 and R2 are independently H, methyl, ethyl, propyl, isopropyl, n-butyl, isobutyl, or phenyl,
   wherein Z is O, S, or NR3 where R3 is H, methyl, ethyl, propyl, isopropyl, n-butyl, isobutyl, or phenyl,
   wherein P is PEG or the PEG like molecule, and
   wherein n is a positive integer ranging from 1 to 100,000.